United States Patent
Brisebrat et al.

(10) Patent No.: US 10,107,724 B2
(45) Date of Patent: Oct. 23, 2018

(54) SYSTEM FOR PIERCING A SEALING MEMBRANE

(71) Applicant: DiaMed GmbH, Cressier FR (CH)

(72) Inventors: Jean-Michel Brisebrat, Villers (FR); Cédric Gagnepain, Riorges (FR); Pascal Barthelon, Nandax (FR)

(73) Assignee: DiaMed GmbH, Cressier (CH)

( * ) Notice: Subject to any disclaimer, the term of this patent is extended or adjusted under 35 U.S.C. 154(b) by 56 days.

(21) Appl. No.: 14/404,213

(22) PCT Filed: May 31, 2013

(86) PCT No.: PCT/FR2013/051231
§ 371 (c)(1),
(2) Date: Nov. 26, 2014

(87) PCT Pub. No.: WO2013/178961
PCT Pub. Date: Dec. 5, 2013

(65) Prior Publication Data
US 2015/0185116 A1 Jul. 2, 2015

(30) Foreign Application Priority Data
May 31, 2012 (FR) ..................................... 12 55032

(51) Int. Cl.
*B67B 7/00* (2006.01)
*G01N 1/28* (2006.01)
(Continued)

(52) U.S. Cl.
CPC ................. *G01N 1/28* (2013.01); *B67B 7/24* (2013.01); *G01N 35/026* (2013.01);
(Continued)

(58) Field of Classification Search
CPC .... B67B 7/24; B67B 7/26; B67B 7/28; B67B 7/00; G01N 1/28; G01N 35/026; B67D 3/043
See application file for complete search history.

(56) References Cited

U.S. PATENT DOCUMENTS

| 4,763,460 A | * | 8/1988 | Higo ........................ B67B 7/24 30/366 |
| 5,096,638 A | * | 3/1992 | Meyke ................ B29C 44/3446 264/211.21 |

(Continued)

FOREIGN PATENT DOCUMENTS

| DE | 2151729 | 4/1973 |
| WO | 2010/116069 | 10/2010 |

OTHER PUBLICATIONS

PCT Search Report for Application No. PCT/FR2013/051231, dated Sep. 13, 2013, 2 pages.

*Primary Examiner* — Kenneth E. Peterson
*Assistant Examiner* — Liang Dong
(74) *Attorney, Agent, or Firm* — Lee & Hayes, PLLC

(57) ABSTRACT

The invention provides a piercing system for piercing at least one sealing membrane (18) closing off at least one cavity (14) of a receptacle, said system including a piercing member (110) configured to puncture the sealing membrane (18) and an ionizing device for removing the electrostatic charges that might be carried by said cavity (14). In accordance with the invention, said ionizing device comprises the piercing member (110) that is adapted to present ionizing properties. The invention also provides a method of piercing at least one sealing membrane (18) closing off at least one cavity (14) of a receptacle, said method comprising piercing the sealing membrane (18) in order to open up said cavity (14), and removing the electrostatic charges that might be carried by said cavity (14), wherein the sealing membrane (Continued)

(18) is pierced and the electrostatic charges is removed by a piercing member (110) adapted to present ionizing properties.

19 Claims, 10 Drawing Sheets

(51) Int. Cl.
*G01N 35/02* (2006.01)
*G01N 35/04* (2006.01)
*G01N 35/10* (2006.01)

(52) U.S. Cl.
CPC ............... *G01N 2035/0405* (2013.01); *G01N 2035/1048* (2013.01); *Y10T 83/0481* (2015.04); *Y10T 83/9314* (2015.04)

(56) References Cited

U.S. PATENT DOCUMENTS

| | | | |
|---|---|---|---|
| 5,667,565 A * | 9/1997 | Gondar | B03C 3/017 15/1.52 |
| 5,949,635 A * | 9/1999 | Botez | H05F 3/06 361/213 |
| 6,464,943 B1 * | 10/2002 | Yiu | B01D 1/14 159/16.1 |
| 2001/0003997 A1 | 6/2001 | Fetcenko et al. | |
| 2006/0174487 A1 * | 8/2006 | Andis | B26B 19/06 30/34.05 |
| 2010/0044581 A1 * | 2/2010 | Fujita | H01T 23/00 250/424 |

* cited by examiner

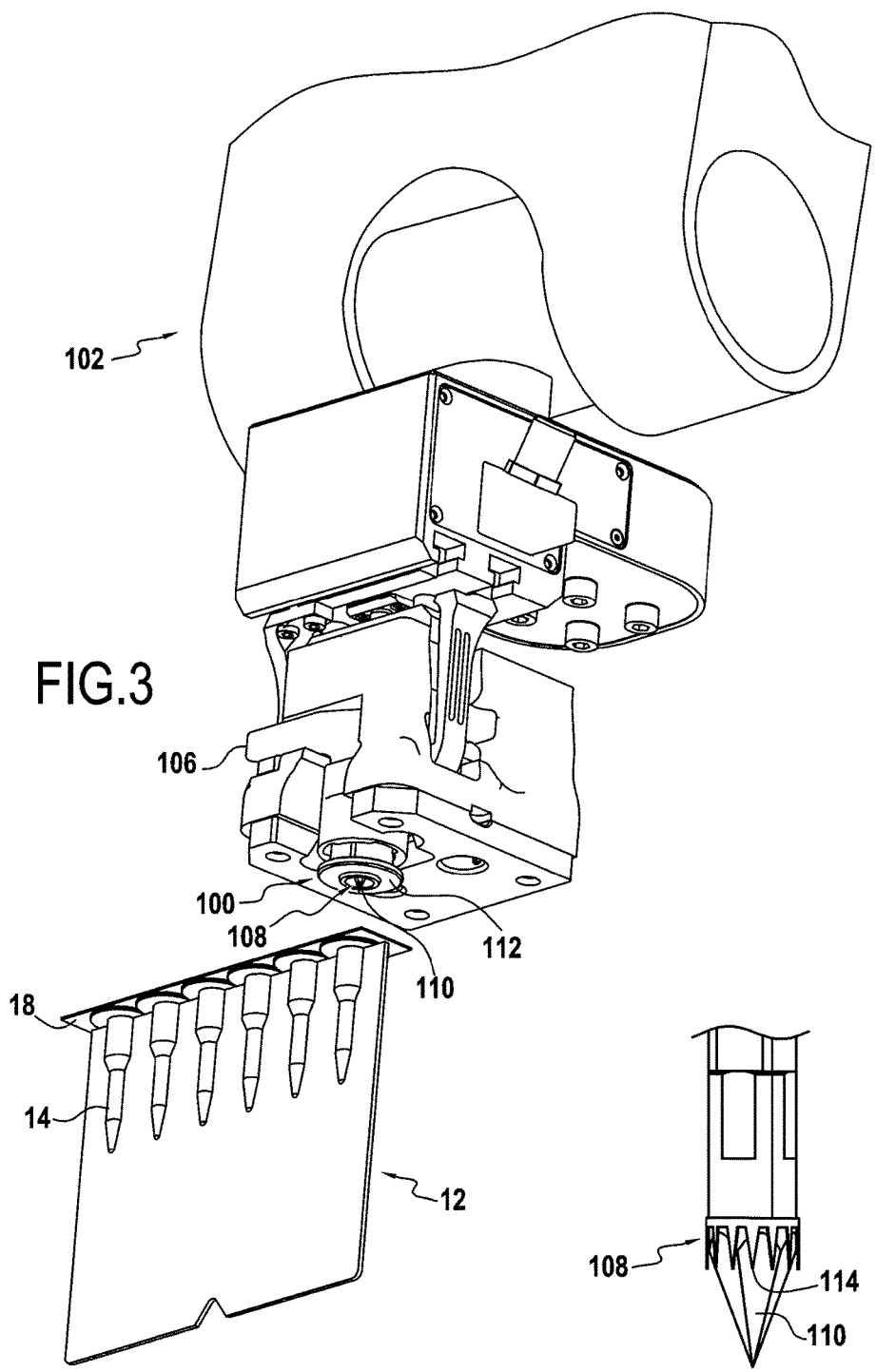

SYSTEM FOR PIERCING A SEALING MEMBRANE

CROSS-REFERENCE TO RELATED APPLICATIONS

This Application is the National Stage of International Application No. PCT/FR2013/051231, filed May 31, 2013, which claims priority to French Patent Application No. 1255032, filed May 31, 2012, the entire disclosures of which are incorporated herein by reference.

The present invention relates to the field of instruments for conducting medical analyses.

Conventionally, such instruments, which may also be referred to as "automated analyzers", make it possible to automate certain protocols, e.g. piercing the sealing membrane of a receptacle, and pipetting liquids, in particular a blood sample, or any other type of human sample, into said receptacle, which initially contains one or more reagents.

The device and the method of the invention are particularly suitable for piercing the sealing membrane of a gel card.

In known manner, a gel card is a receptacle provided with one or more reaction wells, which are initially sealed off by a sealing membrane and each of which contains a reagent, it being possible for the reagent to differ from one well to another in any one gel card.

For filling such a gel card, certain criteria must be satisfied, in particular an air gap must be formed between the metered amount or "dose" of liquid that is dispensed and the reagent that is previously present at the bottom of the well in the gel card. The presence of an air gap temporarily prevents any physical contact between the dispensed dose of liquid and the reagent. An advantage of such an air gap is to control the instant from which the chemical reaction is to start.

Another criterion to be satisfied for filling is that there should be no splashes of liquid on the inside wall of the well, in order to avoid a fraction of the dose of liquid remaining stuck to the walls of the well, and thereby being left out of the reaction mixture that is to be incubated and centrifuged. Such splashes most often come from the dose of liquid that is dispensed into the well being split to various extents but always randomly.

It is now known that formation of splashes on the inside walls of a well can be avoided by removing electrostatic charges from said receptacle. The electrostatic charges carried by the receptacle tend to break up the dose of liquid as it leaves the filling means. As a result, certain fractions of the dose come to be stuck against the inside wall of the well, because of the attraction forces generated by the electrostatic charges. Forming the air gap between the dose of liquid dispensed and the reagent previously present at the bottom of the receptacle is also facilitated by the absence of electrostatic force tending to deflect the dose dropped by the filling means. The Patent Application published under No. WO 2010/116069 describes a method and a device for filling a gel card that is initially closed off by a sealing membrane. The device described includes means for piercing the membrane, and other means designed to remove the electrostatic charges that might be carried by the well of the gel card prior to the dispensing operations.

An object of the present invention is to provide a system that is improved compared with the prior art device.

In particular, an object of the present invention is to provide a system making it possible for a receptacle of the gel card type that is initially closed off by a membrane, before it is filled, to be conditioned even more rapidly and more effectively than with the prior art device.

This object is achieved with a piercing system for piercing at least one sealing membrane closing off at least one cavity of a receptacle, said system including a piercing member configured to puncture the sealing membrane and an ionizing device for removing the electrostatic charges that might be carried by said cavity, said ionizing device comprising the piercing member that is adapted to present ionizing properties.

With the system of the invention, the operation of piercing the sealing membrane closing off the receptacle and the operation of ionizing said receptacle are performed by a single common member that is referred to as an "ionizing device" in the present specification.

Firstly, the ionizing device is adapted to generate a flow of ions of alternately positive and negative charge, this flow of ions being transmitted to the receptacle by ambient air. This alternation of charge signs makes it possible to remove the electrostatic charges carried by the walls of the receptacle.

In addition, the ionizing device is shaped in such a manner as to be capable of piercing the sealing membrane of the receptacle to be filled.

These two operations can thus be performed simultaneously or at least during a single common step.

By means of these provisions, in addition, the ionizing device also comes into contact with the sealing membrane and thus comes very close to the cavity of the receptacle, or indeed penetrates into said cavity. In addition, the axis of the ionizing device can be aligned with the axis of the receptacle. The ionization is thus much more effective and more rapid than in the prior art device, in which the strip of ionization spikes was necessarily remote from the gel card wells and inclined relative to them.

In certain embodiments the piercing member comprises a piercing spike designed to penetrate into the cavity of the receptacle by passing through the sealing membrane.

In certain embodiments, the ionizing device further comprises non-piercing ionizing spikes surrounding the piercing spike.

In certain embodiments, the receptacle is a gel card that includes a plurality of wells closed off by a sealing membrane, each of the wells containing one or more reagents, and the cavity is a well in said gel card.

In an embodiment, the piercing member is connected to a voltage generator. Preferably, the piercing member is adapted to be brought to an electric potential generating corona effect.

The invention also provides a piercing method for piercing at least one sealing membrane closing off at least one cavity of a receptacle, said method comprising piercing the sealing membrane in order to open up said cavity, and removing the electrostatic charges that might be carried by said cavity, wherein the piercing of the sealing membrane and the removal of the electrostatic charges are performed by means of a single common member, namely a piercing member adapted to present ionizing properties.

In accordance with the invention, removing the electrostatic charges (i.e. the ionization) from the cavity of the receptacle is performed during and/or after the piercing.

Generally, the piercing of the sealing membrane and the removal of the electrostatic charges are performed together.

In an implementation, the piercing member and the cavity of the receptacle are placed facing each other, and the piercing member is inserted into the cavity and is then extracted from it, whereby the sealing membrane closing off said cavity is pierced, the piercing member presenting ionizing properties at at least one instant between the start of insertion of the piercing member into the cavity and the end of withdrawal of the piercing member from the cavity.

The piercing member usually comprises a conductive element having ionizing properties when it is brought to an electric potential, in particular to an electric potential generating corona effect. The electric potential applied to the piercing member may be controlled and modulated as needed during performance of the method. The piercing member may thus present ionizing properties at some point in time or continuously.

In an advantageous implementation, the piercing member presents ionizing properties continuously or substantially continuously from the start of insertion of the piercing member into the cavity to the end of withdrawal of the piercing member from the cavity.

In certain implementations, the method comprises at least the following steps in succession:
  placing the piercing member and the receptacle in an entry position;
  inserting the piercing member into the cavity to a pushed-in position in which the sealing membrane is pierced; and
  extracting the piercing member from the cavity and placing the piercing member and the receptacle in an exit position.

An entry position is a position in which the piercing member is situated in the vicinity of the inlet of the cavity, in particular facing said cavity, and more particularly is aligned with the axis of said cavity.

In the same way, an exit position is a position in which the piercing member is situated in the vicinity of the outlet of the cavity, in particular facing said cavity, and more particularly aligned with the axis of said cavity.

In accordance with certain implementations, the method includes:
  placing the piercing member in an entry position above the sealing membrane;
  lowering the piercing member into the cavity to a pushed-in position in which the sealing membrane is pierced; and
  raising the piercing member back up from its pushed-in position to an exit position situated above the cavity.

In accordance with certain implementations, the method includes:
  placing the receptacle in an entry position facing the piercing member;
  moving the receptacle towards the piercing member so that the piercing member penetrates into the cavity to a pushed-in position in which the sealing membrane is pierced; and
  moving the receptacle away from the piercing member by bringing it to an exit position situated facing said piercing member.

In any event, it is possible, in a following step, to move the receptacle away from the piercing member or vice versa.

In certain implementations, the piercing member and the receptacle are maintained in the pushed-in position for a predetermined time.

In certain implementations, inserting the piercing member into the cavity and extracting it from the cavity, i.e. lowering and raising the piercing member or raising and lowering the receptacle are performed in a continuous back-and-forth movement. In other words, the piercing member or the receptacle moves in a continuous back-and-forth movement during which the piercing member is not held stationary in the pushed-in position in the cavity in the receptacle.

In certain implementations, after the sealing membrane has been pierced, the piercing member and the receptacle are held stationary in the exit position for a predetermined time.

In certain implementations, inserting the piercing member (i.e. lowering the piercing member or raising the receptacle from its entry position to its pushed-in position) is performed at a first predetermined speed, and extracting the piercing member (i.e. raising the piercing member or lowering the receptacle from its pushed-in position to its exit position) is performed at a second predetermined speed that may be equal to, less than, or greater than the first predetermined speed.

Various embodiments and implementations are described in the present specification. However, unless otherwise specified, the characteristics described with reference to any one embodiment or implementation may be applied to any other embodiment or implementation.

Other characteristics and advantages of the invention appear on reading the following description of embodiments of the invention that are given by way of non-limiting example. This description is given with reference to the accompanying sheets of drawings, in which:

FIG. 3 is a detail view of a first embodiment of the piercing system of the invention;

FIG. 5 is a detail view of a variant of the first embodiment of the ionizing device of the invention;

FIG. 1 is a diagrammatic view of an example of an automated medical analyzer 10.

Figure 2:
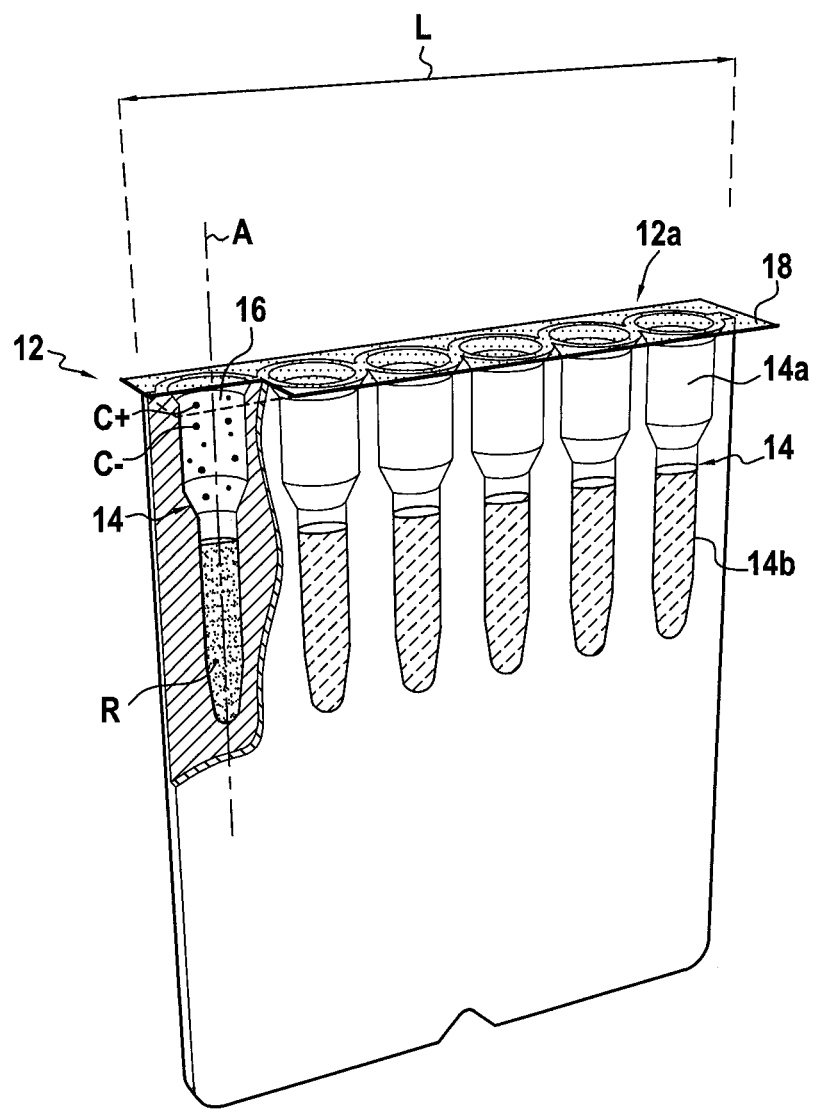
FIG. 2 is a front view of a receptacle of the gel card type that is designed to be used with the automated analyzer of FIG. 1.

This automated medical analyzer 10 manipulates gel cards. As shown in FIG. 2, a gel card 12 is provided with a plurality of wells or cavities 14, in particular with six wells, opening out in a top wall 12a of said gel card. These wells 14 have openings 16 formed in the top wall 12a of the gel card 12, said openings 16 being initially sealed off by a sealing membrane 18 extending in a longitudinal direction L of the gel card 12. In the example, the sealing membrane 18 is a long thin strip sealed to the top wall of the gel card 12.

Each well 14 of said gel card 12 is filled with reagent R, it being possible for said reagent R to be different from one well to another in the gel card 12. In addition, each well 14 is formed by a top cavity 14a of substantially cylindrical shape that is connected to a bottom cavity 14b that is also of substantially cylindrical shape via a frustoconical intermediate cavity. The top cavity 14a has a diameter that is significantly greater than the diameter of the bottom cavity 14b, the bottom and top cavities being in mutual alignment along a common axis A. The level of reagent is situated slightly below the top end of the bottom cavity 14b, while the top cavity 14a, which is initially empty, opens out in the top wall 12a of the gel card 12.

With reference, once again, to FIG. 1, it can be observed that the automated analyzer 10 includes a first embodiment of the piercing system 100 of the invention that is mounted on a poly-articulated robot 102 at the distal end (or "end member") 106 of the arm thereof, a filling device 200 for filling gel cards, a monitoring station 300 for verifying the positioning of the liquid poured into the wells 14 by the filling device 200, a centrifuge 400, and means 500 for analyzing the chemical reactions that can take place in the wells 14 of the gel card 12, such means being constituted, in particular, by a viewing station.

Gel cards 12 are made of plastics material and they tend to carry electrostatic charges $C^+$ and $C^-$ (see FIG. 2).

Before inserting the samples to be analyzed into a well 14 chosen for performing the analysis, and for the reasons already mentioned above, the portion of membrane 18 that is situated above the well 14 needs to be punctured and the well 14 needs to be ionized in order to remove the electrostatic charges.

With the first embodiment of the piercing device 100 of the invention that is described in more detail with reference to FIGS. 3, 4A, 4B, and 4C, the piercing and ionizing operations are performed using a single common member, and generally together. However, this implementation is not limiting, and, alternatively or additionally, the ionizing operation may also be performed after the piercing operation.

As show in FIG. 3, the piercing system 100 includes an ionizing device 108 provided with a spike 110 forming a piercing member and fastened in detachable manner to a cylindrical sleeve 112, this enabling said spike 110 to be cleaned regularly.

In accordance with the invention, the piercing spike 110 performs both the operation of piercing the portion of membrane 18 that is situated above the well 14, and also the operation of ionizing said well 14.

In order to ionize said well 14, the piercing spike 110 is adapted to be brought to an electrical potential that generates corona effect that removes the electrostatic charge carried by the gel card. In this example, the piercing spike 110 generates an electric field E at the wells of the gel card. For this purpose, it is possible to choose, for example, for the piercing spike 110, a power supply delivering an almost sinusoidal wave having a frequency of 250 hertz (Hz), a minimum potential difference of 4.2 kilovolts (kV), and capable of delivering a current of less than 3.5 milliamps (mA).

The absence of electric arcing also enables the ionizing device 108 to be in contact with the gel card 12.

In the example shown, the piercing spike 110 has an outside diameter substantially equal to the inside diameter of the top cavity 14a of the well in the gel card 12. However, this example is not limiting, and the outside diameter of the piercing spike 110 may be significantly less than the inside diameter of the top cavity 14a of the well 14 in the gel card.

In addition, the piercing spike 110 may be provided with beveled facets 110a. It is possible to adjust the number of beveled facets 110a of the piercing spike 110 and the inclination of said beveled facets 110a relative to the main axis of the piercing spike 110, as a function of the nature of the material of which the sealing membrane 18 is made.

In a variant of the invention, non-piercing ionizing spikes 114 may be positioned in a ring configuration around the piercing spike 110 as shown in FIG. 5, this making it possible to reinforce the effectiveness of the ionizing of the well 14 in the gel card 12.

The method of the invention for piercing the sealing membrane 18 of a gel card 12 is described below with reference to FIGS. 4A to 4C.

Figure 4A:
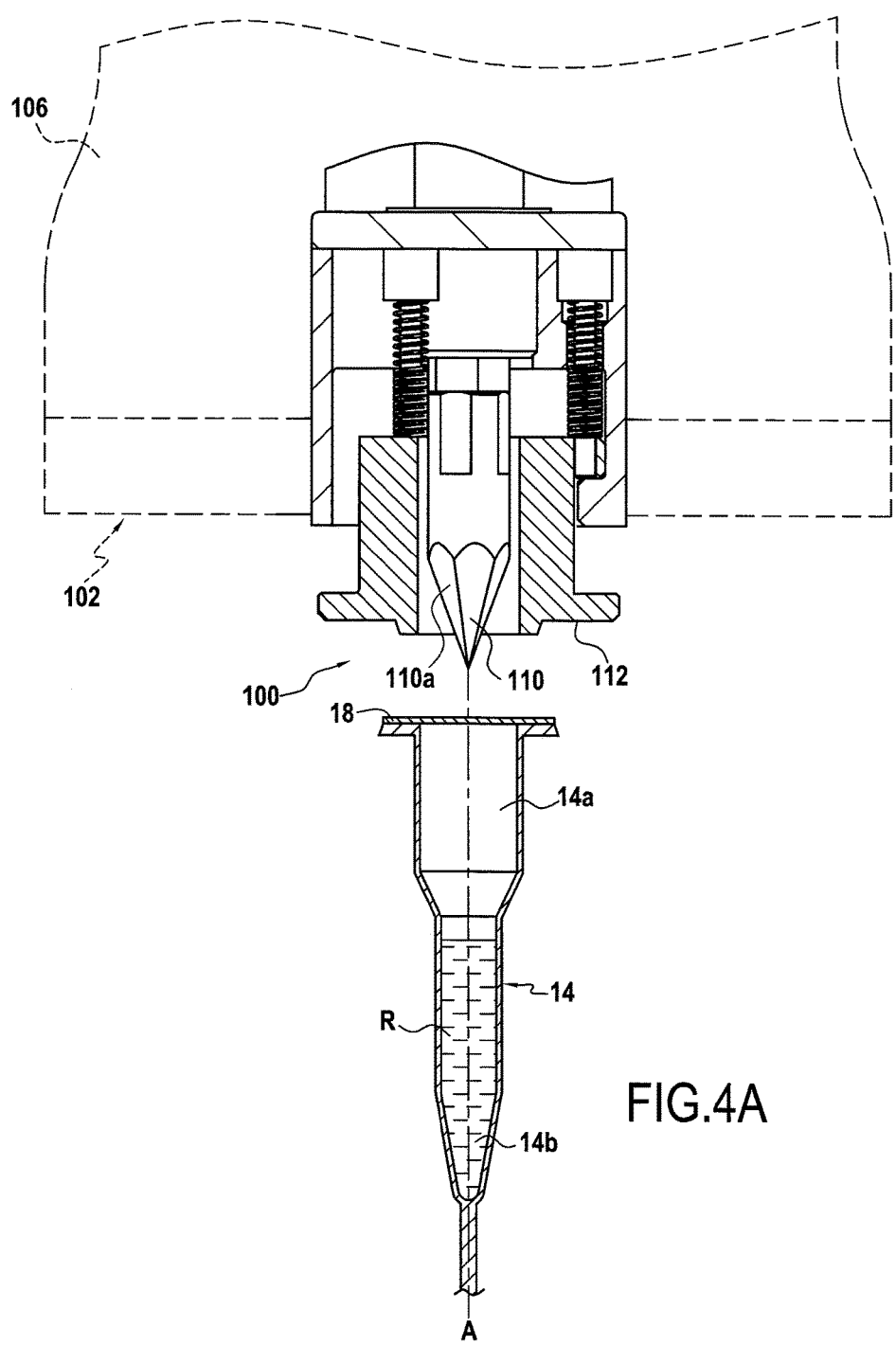
FIG. 4A is a section view of the first embodiment of the piercing system of the invention, showing the piercing member in the fully retracted position.

During a first step, the piercing spike 110 is firstly aligned with the axis A of the well 14 of the gel card 12 as shown in FIG. 4A. At this instant, the piercing spike 110 is placed in an "entry" position above the sealing membrane 18.

Figure 4B:
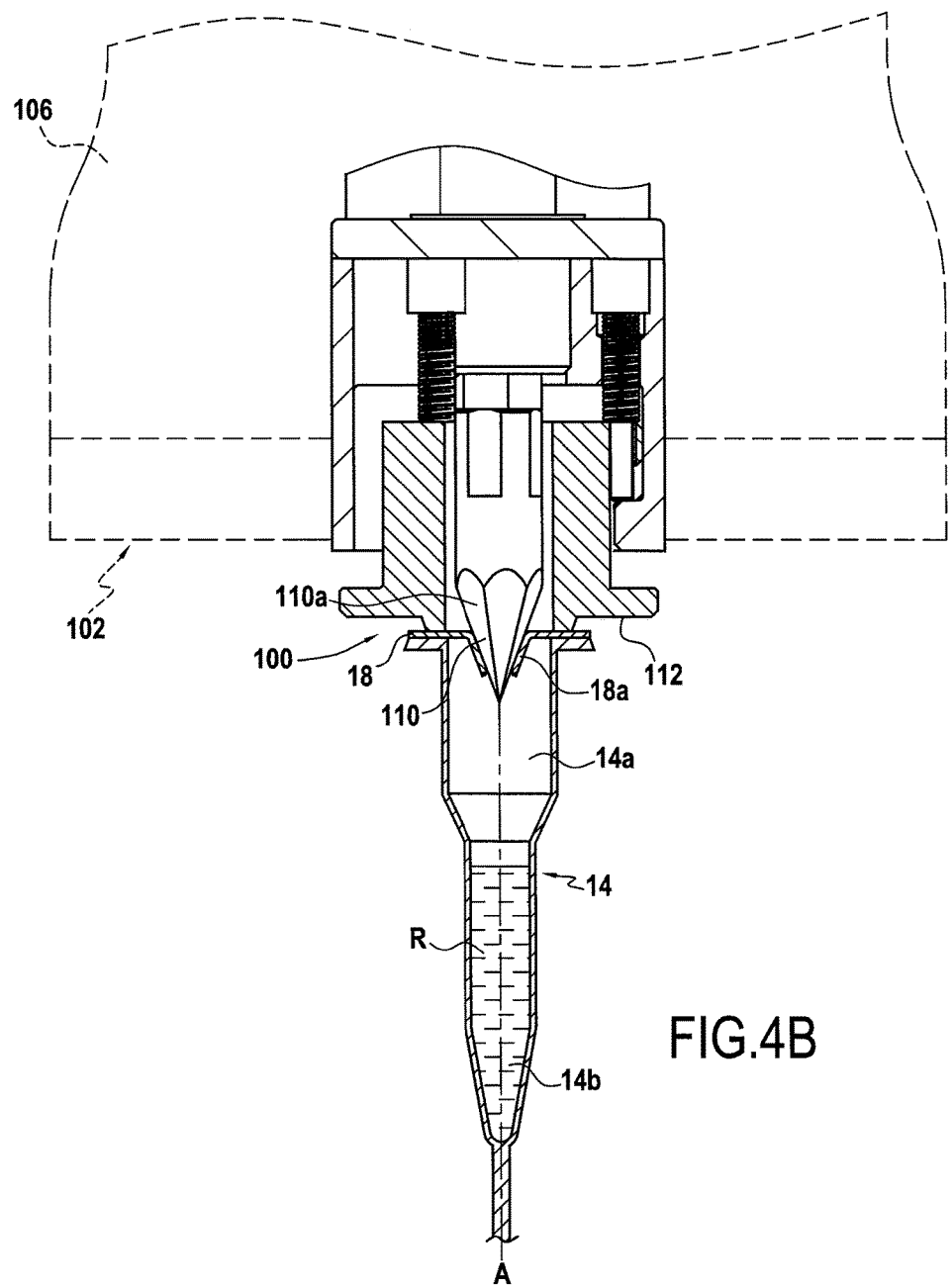
FIG. 4B is a section view of the start of piercing of the sealing membrane of the gel card by the first embodiment of the piercing system of the invention.
Figure 4C:
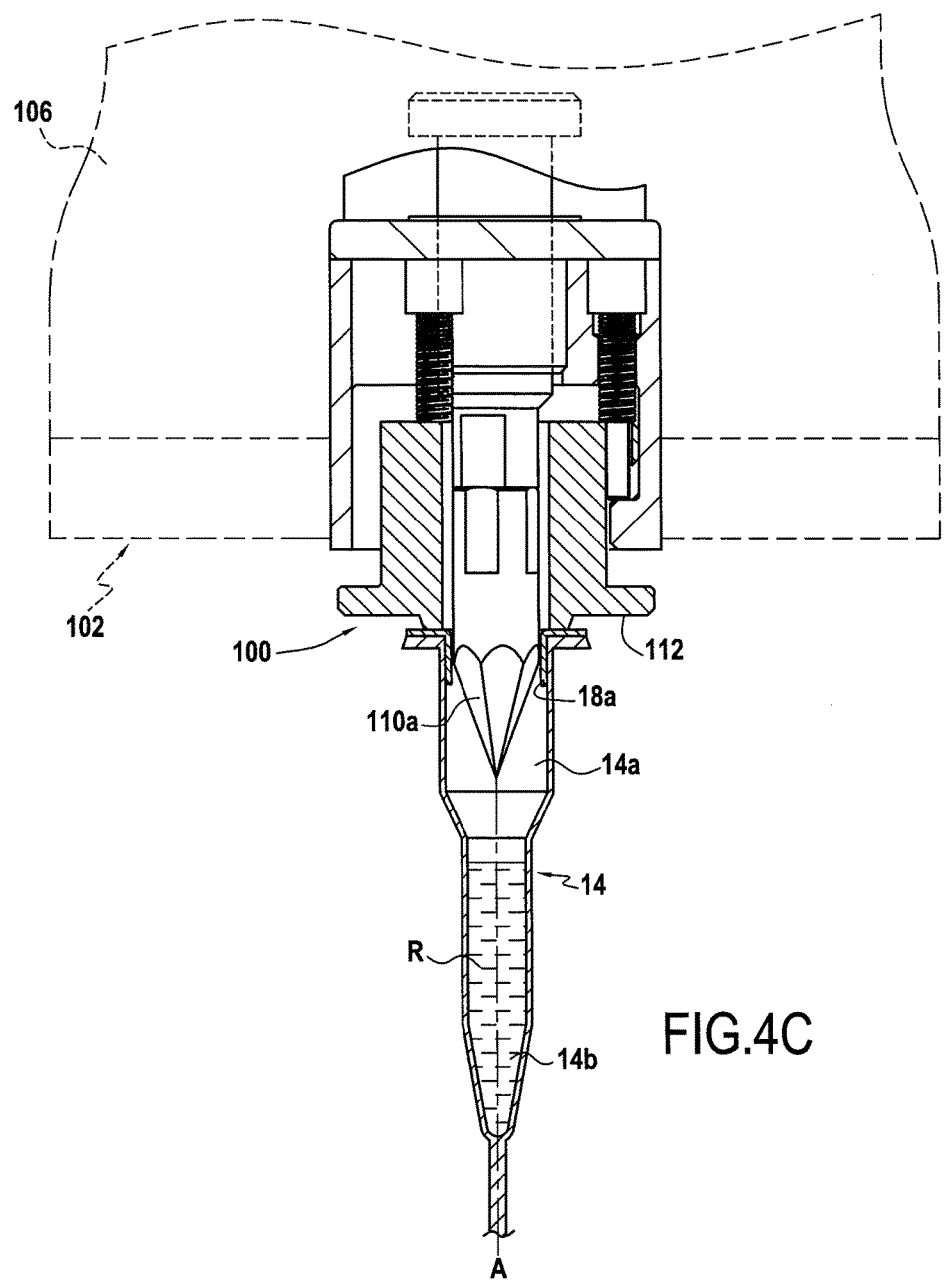
FIG. 4C is a section view of the first embodiment of the piercing system of the invention with the piercing member in the pushed-in position.

In a second step of the method, as shown in FIGS. 4B and 4C, the piercing spike 110 is lowered into the top cavity 14a of the well 14 in a movement in vertical translation until it is in a "pushed-in" position in which the membrane 18 is completely pierced. It can be noted that the sleeve 112 comes to be positioned in abutment on either side of the well 14 on the top wall 12a.

As indicated above, the piercing spike 110 has an outside diameter substantially equal to the inside diameter of the top cavity 14a of the well in the gel card 12. Thus, as shown in FIGS. 4B and 4C, while the sealing membrane of the well 14 is being pierced, the piercing spike 110 slides along the walls of the top cavity 14a of the well, pushing back the pierced portion of membrane 18a along the walls of said top cavity 14a. In this situation, since the piercing spike 110 is in contact with the sealing membrane 18, the close environment around the piercing spike 110 benefits from the residual effect of the ionization.

The piercing spike 110 comes both to puncture the portion of membrane 18 of the gel card 12 that is situated above the well 14, and also to ionize the well 14.

In a third step, the piercing spike 110 is then raised back up from its pushed-in position to its exit position situated above the well 14.

Preferably, the piercing spike 110 is brought to an electric potential generating corona effect making it possible to remove the electrostatic charges carried by the gel card continuously, throughout the piercing operation (i.e. during the second and third steps).

Finally, in a fourth step, the piercing spike 110 is moved away from the gel card 12, optionally in order to reiterate the above-mentioned steps on another well of the gel card 12.

Thus, the piercing method of the invention makes it possible both to pierce the sealing membrane 18 of a well 14 of the gel card 12 and also to ionize said well 14. This is particularly advantageous for gel cards 12 that are used partially during analyses. In some cases, certain wells are used for a first analysis and other wells are used for a second analysis. For each analysis, it is, however, necessary to guarantee the quality of the reagent R present in the well 14 of the gel card 12. It is thus recommended for the wells 14 to be opened at the last minute, just before they are filled.

In an implementation of the piercing method of the invention, the piercing spike 110 may be held stationary in its pushed-in position for a predetermined time, e.g. for one second.

In another implementation of the piercing method, the piercing spike 110 can also be lowered and raised in a continuous back-and-forth movement. The spike is then not held stationary in the pushed-in position.

In advantageous manner, after the portion of membrane that is situated above the chosen well 14 has been pierced, the piercing spike 110 can be held stationary in its exit position for a predetermined time, such as, for example, one second. This implementation gives good results as regards forming an air gap between the dispensed dose of liquid and the reagent.

Formation of the air gap is further facilitated when the piercing spike 110 is lowered from its entry position to its pushed-in position at a first predetermined speed, and when it is raised back up to is exit position at a second predetermined speed that is less than said first predetermined speed. For example, the piercing spike 110 can then be raised from its pushed-in position to its exit position in one second, the piercing operation having been performed in a time less than one second.

Figure 1:
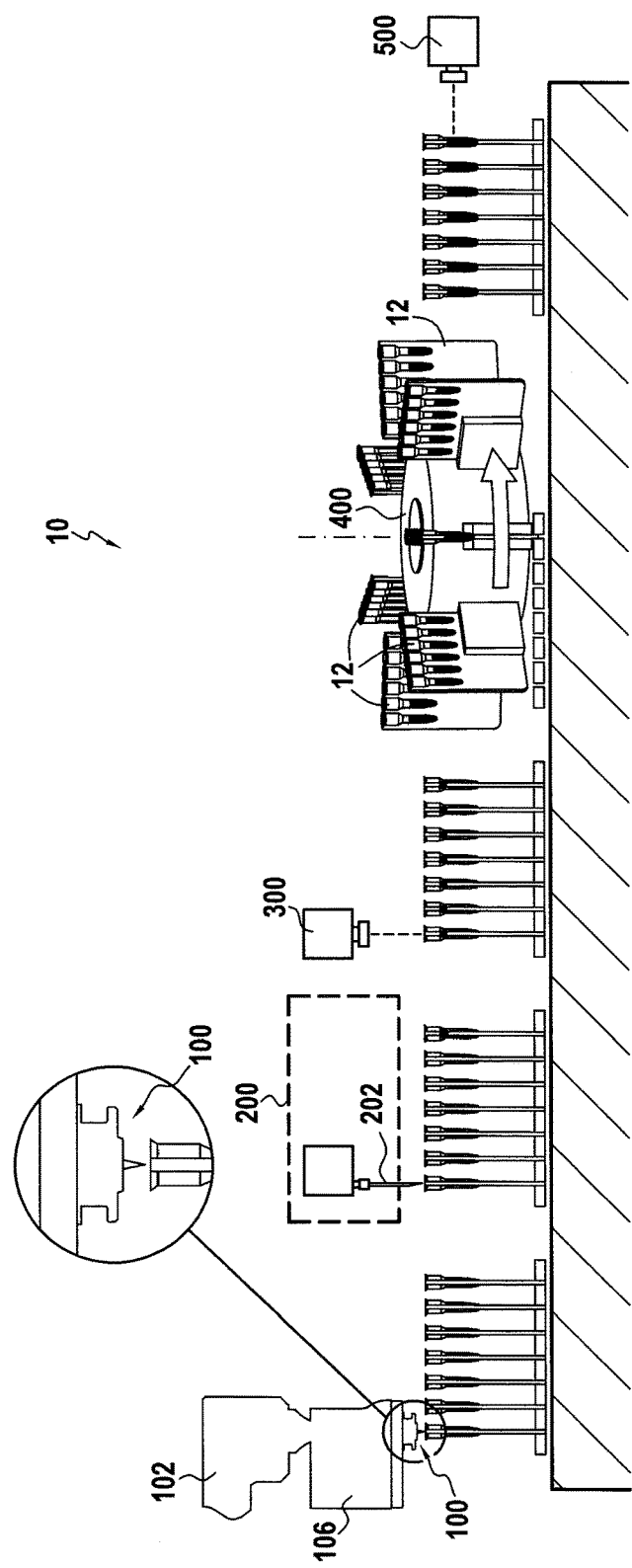
FIG. 1 is a diagrammatic view of an automated medical analyzer that is adapted to process samples taken from humans, and that includes a poly-articulated robot provided with a first embodiment of a piercing system of the invention.

As shown in FIG. 1, after the piercing and ionization operation, the gel card 12 is generally brought towards the filling means 200. These filling means 200 comprise at least one pipette 202 that is inserted into the top cavity 14a of the well 14 via the hole formed in the sealing membrane 18, so as to pour a dose of liquid into it. Preferably, as indicated above, provision is made to create an air gap between the reagent and the poured-in dose.

Then, after the filling step, the gel card 12 is brought to the monitoring station 300 in order to check that air gaps are present. Then, the gel card 12 is incubated and centrifuged using the centrifuge 400. Finally, the result of the chemical reactions is analyzed using the means 500 for analyzing chemical reactions.

A second embodiment of the piercing system of the invention is described with reference to FIGS. 6 to 7C. The second embodiment of the invention differs from the first embodiment mainly in that the piercing system 600 is stationary in the automated medical analyzer 10, and in that the gel card 60, manipulated by the automated medical analyzer 10, is mounted to move relative to the piercing system 600.

Figure 6:
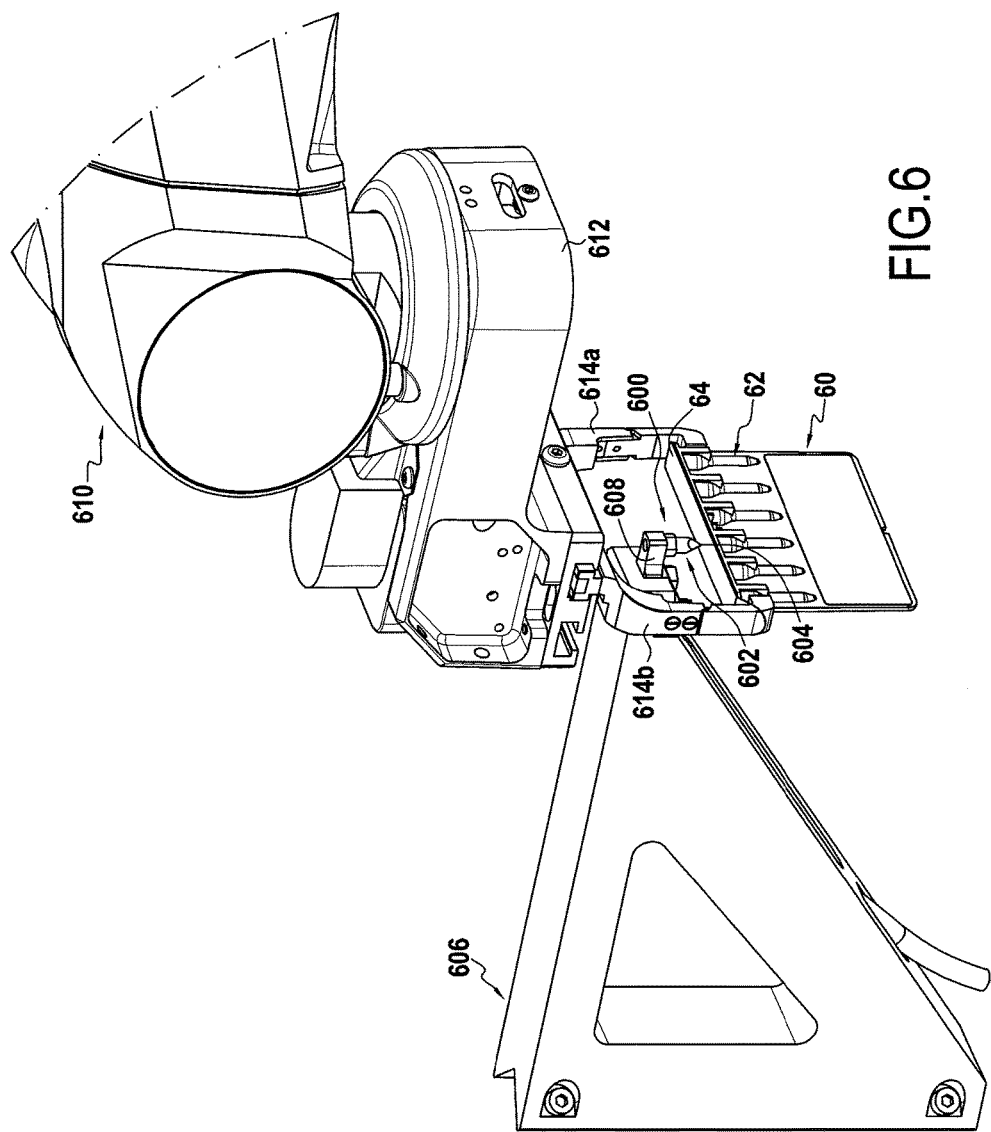
FIG. 6 is a detail view of a second embodiment of the piercing system of the invention.

The gel card 60 shown in FIG. 6 is substantially identical to the gel card in the first embodiment and is therefore not described in detail below. Unless otherwise indicated, all of the characteristics of the above-described gel card remain valid for the second embodiment.

In the same way as with the first embodiment of the piercing system 100, the operations of piercing and of ionizing the wells 62 of the gel card 60 are, in this example, performed by a single common member.

FIG. 6 shows the piercing system 600 that includes an ionizing device 602 provided with a spike 604 forming a piercing member. In the example shown, the piercing spike 604 is fastened to a mounting 608 that is itself fastened detachably to a support 606, which is a set square in this example, secured to the frame of the automated analyzer 10. Mounting the piercing system 600 is thus simple and it can be readily incorporated into the automated medical analyzer 10. The detachable mounting of the piercing spike 604 also enables it to be cleaned regularly.

As in the first embodiment, the piercing spike 604 is adapted to be brought to an electric potential that continuously generates corona effect.

The gel card 60 can be moved relative to the piercing system by means of a poly-articulated robot 610 of the automated analyzer 10. As shown in FIG. 6, the gel card 60 is taken hold of at its two ends by jaws 614a, 614b that are substantially L-shaped and that form, in part, the end member 612 of the poly-articulated robot 610.

The method of piercing the sealing membrane 64 of a gel card 60 using the above-mentioned piercing system differs from the piercing method described with reference to FIGS. 4A to 4C only in that the receptacle is mounted to move while the piercing member is stationary.

Figure 7A:
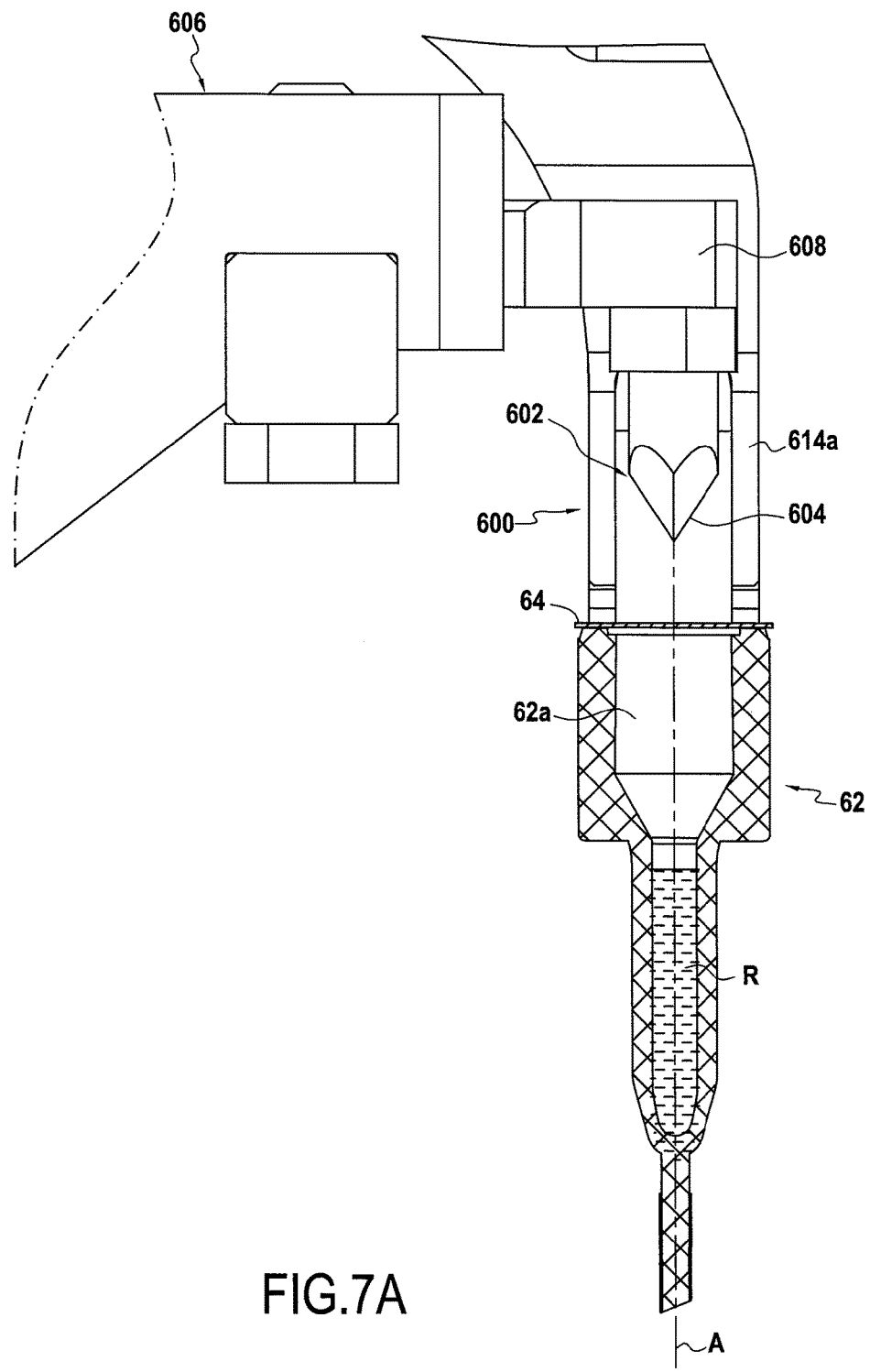
FIG. 7A is a section view of the second embodiment of the piercing system of the invention, showing the receptacle of the gel card type in the entry position below the piercing member.

Thus, in a first step shown in FIG. 7A, the gel card 60 is moved by the poly-articulated robot 610 to an entry position in which it is placed below the piercing spike 604, the axis A of the well 62 of the card being aligned with the piercing spike 604.

Figure 7B:
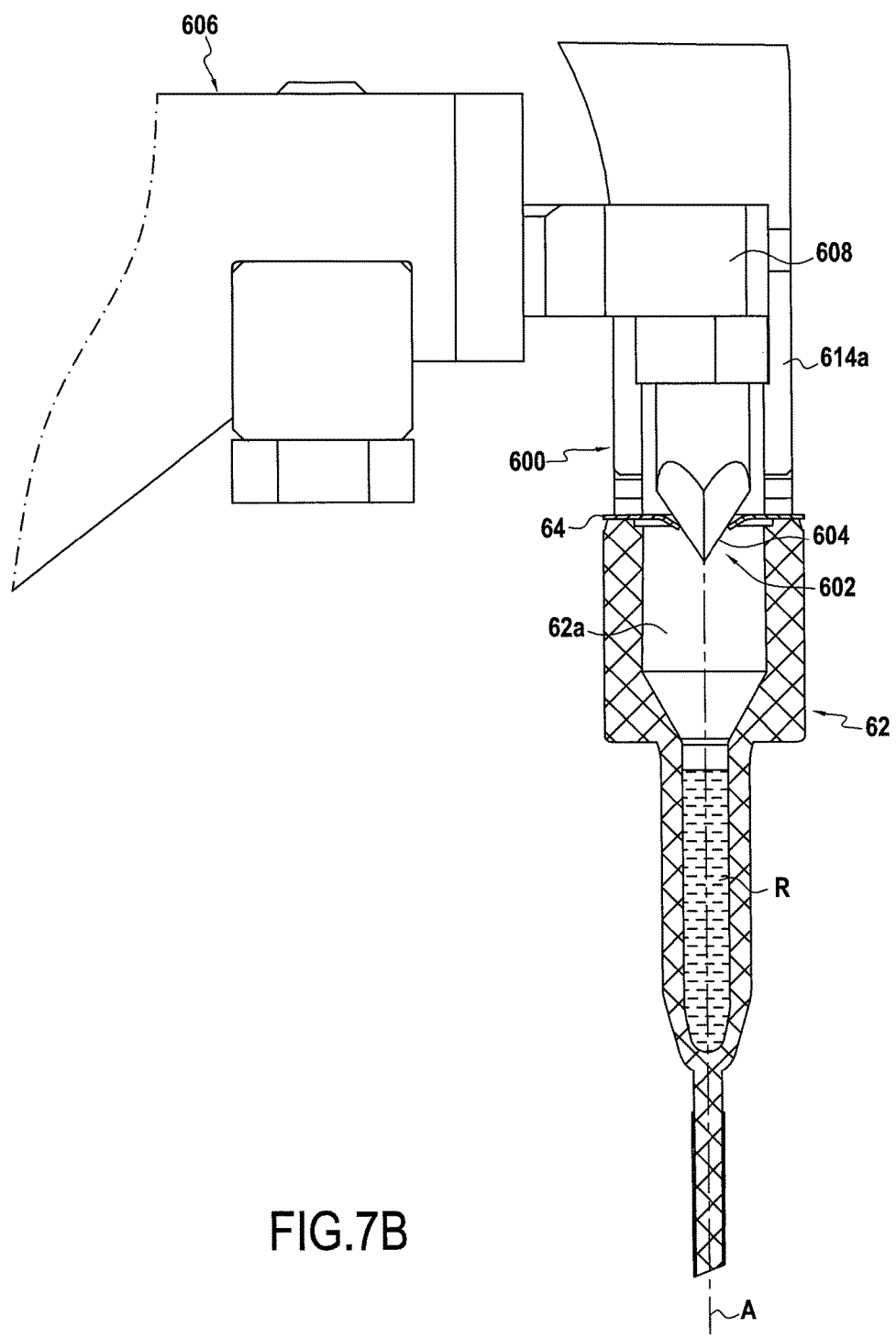
FIG. 7B is a section view of the start of piercing of the sealing membrane of the gel card by the second embodiment of the piercing system.
Figure 7C:
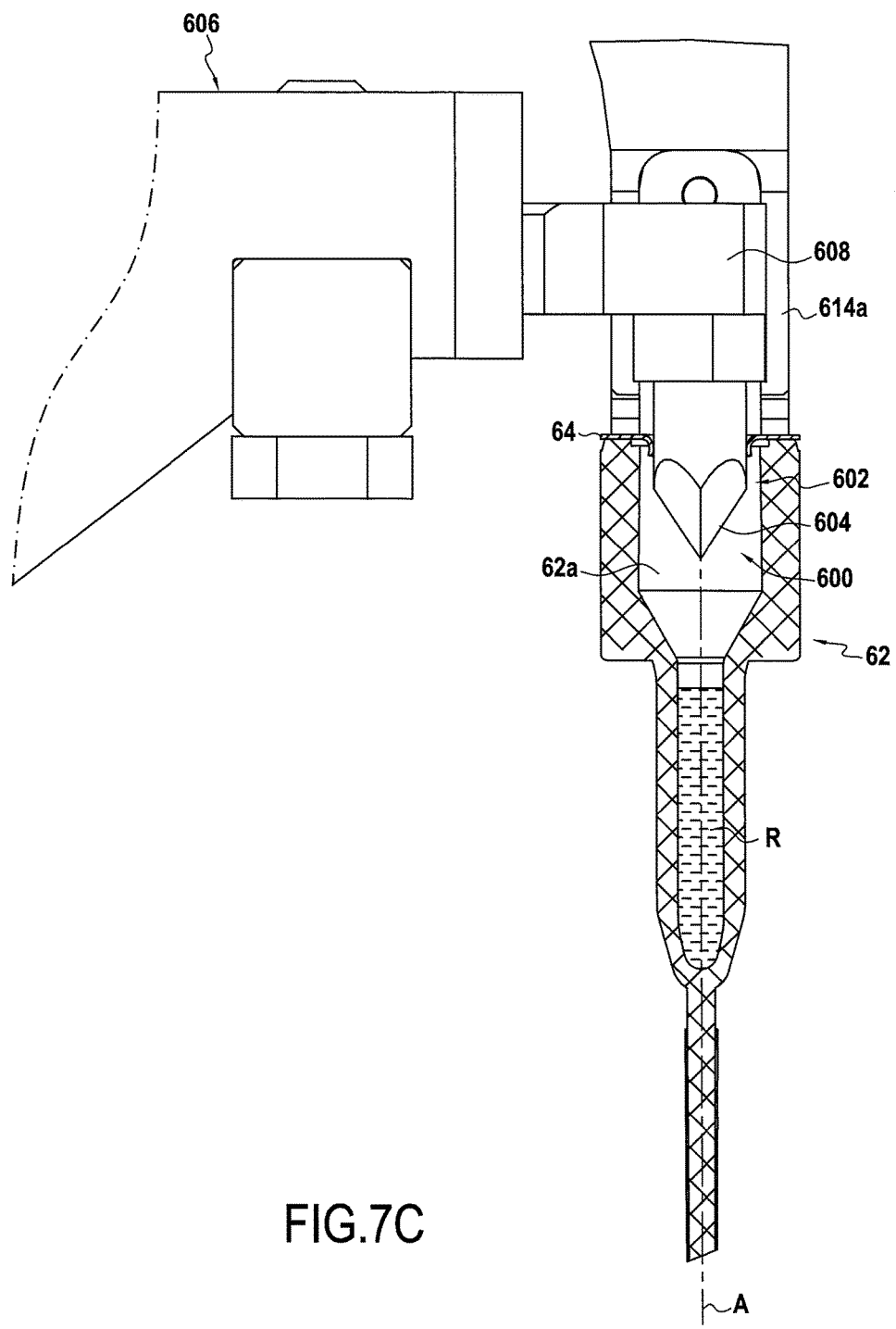
FIG. 7C is a section view of the second embodiment of the piercing system of the invention with the receptacle in the pushed-in position.

In a second step of the method, as shown in FIGS. 7B and 7C, the gel card 60 is moved towards the piercing spike 604 in a movement in translation (vertical translation in this example) until it is in a pushed-in position in which the membrane 64 is pierced.

It should be noted that, in this example, the diameter of the piercing spike 604 is significantly less than the diameter of the top cavity 62a of the gel card 60. In other examples, the diameter of the piercing spike 604 could be even smaller or substantially equal to the diameter of the top cavity 62a of the gel card 60.

The gel card 60 is finally lowered from its pushed-in position to its exit position situated below the piercing spike 604.

Generally, the operations of piercing and of ionizing the well 62 take place together and, more particularly, the ionization is performed throughout the piercing operation. But this implementation is not limiting and the ionization may, for example, be performed during and after the piercing operation or only after the piercing operation.

The various sequencing configurations of the piercing operation that are described with reference to the first embodiment are also applicable to this second embodiment.

Thus, provision may be made for the gel card 60 to be held stationary in its pushed-in position and/or in its exit position for a predetermined time, or, conversely, for its movement inside the top cavity 62a to take place in a continuous back-and-forth movement, or for the speed at which it is pushed onto the piercing spike 604 to be higher than the speed at which it is withdrawn therefrom.

Although the present invention is described with reference to specific embodiments and implementations, it is clear that various modifications and changes may be made to these examples without going beyond the general scope of the invention as defined by the claims. In particular, individual characteristics of the various embodiments and implementations shown/mentioned may be combined in additional embodiments and implementations. Therefore, the description and the drawings should be considered as being given illustratively rather than restrictively.

The invention claimed is:

1. A piercing system for piercing at least one sealing membrane closing off at least one cavity of a receptacle, said system comprising:
    an ionizing device configured to generate a flow of ions of alternately positive and negative charge to remove electrostatic charges carried by said at least one cavity;
    a piercing member configured to puncture the sealing membrane, the piercing member forming an ionizing electrode of the ionizing device; and
    an arm configured to move the receptacle relative to the piercing member, wherein:
        said piercing system is configured to puncture the sealing membrane by moving the receptacle toward the piercing member, with the arm, while maintaining the piercing member stationary.

2. A piercing system according to claim 1, wherein the piercing member comprises a piercing spike designed to penetrate into the cavity of the receptacle by passing through the sealing membrane.

3. A piercing system according to claim 1, wherein the receptacle is a gel card that includes a plurality of wells closed off by a sealing membrane, each of the wells containing one or more reagents, and wherein the cavity is a well in said gel card.

4. A piercing system according to claim 1, in which the piercing member is configured to tolerate an electric potential intended to induce a corona effect.

5. A piercing system according to claim 1,
the piercing member comprising a plurality of beveled facets inclined relative to a central longitudinal axis of the piercing member, the plurality of beveled facets forming a distal tip of the piercing member configured to puncture the sealing membrane,
the piercing member further comprising a plurality of non-piercing members arranged in a ring around the plurality of beveled facets, the plurality of non-piercing members:
extending distally, from proximate a proximal end of the plurality of beveled facets, in a direction substantially parallel to the central longitudinal axis, and
configured to assist in removing electrostatic charges carried by said at least one cavity.

6. A piercing system according to claim 1, further comprising:
a system frame;
a support connected to the frame; and
a mounting detachably fastened to the support, the piercing member being detachably fastened to the mounting.

7. A piercing system according to claim 6, the arm further comprising a first substantially L-shaped jaw, and a second substantially L-shaped jaw disposed opposite the first jaw, the first and second jaws being configured to move the receptacle, in a first direction, toward the piercing member.

8. A piercing system according to claim 7, wherein:
the first jaw is moveable in a second direction perpendicular to the first position,
movement of the first jaw in the second direction assists in clamping a gel card, within which the receptacle is disposed, between the first jaw and the second jaw, and
moving the receptacle in the first direction includes moving the gel card in the first direction.

9. A piercing method for piercing at least one sealing membrane closing off at least one cavity of a receptacle, said method comprising:
piercing the sealing membrane in order to open up said cavity, and
removing any electrostatic charges carried by said cavity, wherein:
the piercing of the sealing membrane and the removal of the electrostatic charges are performed by a single ionizing piercing member, and
piercing the sealing membrane includes moving the receptacle toward the piercing member while maintaining the piercing member stationary.

10. A piercing method according to claim 9, wherein the piercing of the sealing membrane and the removal of the electrostatic charges are performed together.

11. A piercing method according to claim 9, comprising at least the following steps in succession:
placing the piercing member in an entry position above the sealing membrane;
lowering the piercing member into the cavity to a pushed-in position in which the sealing membrane is pierced; and
raising the piercing member back up from its pushed-in position to an exit position situated above the cavity.

12. A piercing method according to claim 9, comprising at least the following steps in succession:
placing the receptacle in an entry position facing the piercing member;
moving the receptacle towards the piercing member so that the piercing member penetrates into the cavity to a pushed-in position in which the sealing membrane is pierced; and
moving the receptacle away from the piercing member by bringing it to an exit position situated facing said piercing member.

13. A piercing method according to claim 9, said method comprising charging the piercing member to an electric potential configured to generate a corona effect.

14. A piercing method according to claim 9, comprising at least the following steps in succession:
placing the piercing member and the receptacle in an entry position;
inserting the piercing member into the cavity to a pushed-in position in which the sealing membrane is pierced; and
extracting the piercing member from the cavity and placing the piercing member and the receptacle in an exit position.

15. A piercing method according to claim 14, wherein the piercing member presents ionizing properties continuously or substantially continuously from the start of insertion of the piercing member into the cavity to the end of withdrawal of the piercing member from the cavity.

16. A piercing method according to claim 14, wherein the piercing member and the receptacle are maintained in the pushed-in position for a predetermined period.

17. A piercing method according to claim 14, wherein inserting the piercing member into the cavity and extracting it from the cavity are performed in a continuous back-and-forth movement.

18. A piercing method according to claim 14, wherein, after the sealing membrane has been pierced, the piercing member and the receptacle are held stationary in the exit position for a predetermined period.

19. A piercing method according to claim 14, wherein inserting the piercing member is performed at a first predetermined speed, and the piercing member is extracted at a second predetermined speed that is less than, equal to, or greater than the first predetermined speed.

* * * * *